(12) United States Patent
Fontana et al.

(10) Patent No.: US 8,624,051 B2
(45) Date of Patent: Jan. 7, 2014

(54) PROCESS FOR THE PREPARATION OF ISOSERINE DERIVATIVES

(75) Inventors: Gabriele Fontana, Milan (IT); Maria Luisa Gelmi, Milan (IT); Federico Gassa, Catiglione Olona (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 13/640,866

(22) PCT Filed: Apr. 13, 2011

(86) PCT No.: PCT/EP2011/055762
§ 371 (c)(1),
(2), (4) Date: Dec. 12, 2012

(87) PCT Pub. No.: WO2011/128353
PCT Pub. Date: Oct. 20, 2011

(65) Prior Publication Data
US 2013/0090493 A1 Apr. 11, 2013

(30) Foreign Application Priority Data
Apr. 15, 2010 (EP) .................................... 10160022

(51) Int. Cl.
*C07C 227/32* (2006.01)
(52) U.S. Cl.
USPC .......................................................... 560/39
(58) Field of Classification Search
USPC .......................................................... 560/39
See application file for complete search history.

(56) References Cited

PUBLICATIONS

Dixon et al. (Highly Diastereoselective Lithium Enolate Aldol Reactions of Butane-2,3-diacetal Desymmetrized Glycolic Acid and Deprotection to Enantiopure anti-2,3-Dihydroxy Esters, Organic Letters, vol. 3, No. 23, pp. 3749-3752).*
Dixon, et al, "Highly Diastereoselective Lithium Enolate Aldol Reactions of Butane-2, 3-diacetal Desymmetrized Glycolic Acid and Deprotection to Enantiopure anti-2, 3-Dihydroxy Esters," Organic Letters, vol. 3, No. 23, pp. 3749-3752, 2001 (XP002596681).
Kise, et al., "Diastereoselective Synthesis of 3-Amino-2-Hydroxyalkanoic Acid Derivatives," Tetrahedron Letters, vol. 36, No. 6, pp. 909-912, 1995 (XP004028703).
Wang, et al., "Highly Diastereoselective Enolate Addition of O-Protected α-Hydroxyacetate to (SR)-tert-Butanesulfinylimines: Synthesis of Taxol Side Chain," Journal of Organic Chemistry, vol. 71, No. 4, pp. 1588-1591, 2006 (XP002596680).
Xiaoxiang, et al., "Palladium-Catalyzed Arylation of Trimethylsilyl Enolates of Esters and Imides. High Functional Group Tolerance and Stereoselective Synthesis of α-Aryl Carboxylic Acid Derivatives," Journal of The American Chemical Society, vol. 126, No. 4, pp. 5182-5191, 2004 (XP002381176).

* cited by examiner

*Primary Examiner* — Johann R Richter
*Assistant Examiner* — Blaine G Doletski
(74) *Attorney, Agent, or Firm* — Lucas & Mercanti, LLP

(57) ABSTRACT

This invention relates to a "one pot" process for the preparation of isoserine derivatives in high diastereoselective way. The process according to the invention includes the steps of reacting a protected glycidic acid with imines to yield isoserines protected both at the —OH and at the —COOH groups, deprotection of the obtained intermediates to isoserines or isoserine 1-4C— alkyl esters. Pure threo derivatives as the main isomer are obtained.

9 Claims, No Drawings

PROCESS FOR THE PREPARATION OF ISOSERINE DERIVATIVES

This application is a U.S. national stage of PCT/EP2011/055762 filed on Apr. 13, 2011, which claims priority to and the benefit of European Application No. 10160022.9, filed on Apr. 15, 2010, the contents of which are incorporated herein by reference.

This invention relates to a "one pot" process for the preparation of isoserine derivatives in high diastereoselective way.

BACKGROUND OF THE INVENTION

α-Hydroxy-β-amino acids (isoserines) are important targets because these amino acids are present in molecules of great biological interest such as the new lipopeptidic siderophore named ornicorrugatin,[1] KRI-1314,[2] a potent human renin inhibitor polypeptide, amastatin,[3] a tetrapeptide with immunoregulatory, antitumor, and antibacterial activity, microginin,[4] threo-β-benzyloxyaspartate (TBOA),[5] the 1st non-transportable blocker for all subtypes of EAATs and, most of all, in taxan derivatives[6].

From the steric point of view, the biological requests of the above amino acids are well defined and the threo (2R,3S) isomers are in general active and thus preferred.

Synthetic approaches for the preparation of compounds of isoserines through the C-2/C-3 bond formation are known by reaction of a sulfinylimine with the litium enolate of a protected α-hydroxy-ester[7a,b] or of a simple imine with the litium enolate of an ester followed by an oxidative process.[7c] The main drawback of the above reactions are in the first case[7a,b] the use of expensive sulfinylimines whose synthesis is not easy. In the second case only moderate yields are obtained and an oxidative step with an expensive reagent (oxaziridine) is required to introduce the α-hydroxy group. According to another synthetic approach[7d], simple imine derivatives are made to react with α-methoxyketene silylacetal in acidic conditions. Isoserine compounds, functionalized with a α-OMe group are formed in moderate yield and diastereoselection. Furthermore the α-OMe group must be deprotected in a separate step. Finally, the condensation of N-arylimines with dangerous aryldiazoacetates in high stoichiometric excess and promoted by an expensive rhodium catalyst is known.[7e] Isoserine derivatives are obtained with variable diastereoselection depending on the substitution pattern and in moderate yields. A major difficulty which affects all the known synthetic methods is to obtain a pure enantiomer because all methods, except rif. 7d, use a chiral auxiliary in the starting reagent/s, thus generating four diastereoisomers in the condensative process.

DESCRIPTION OF THE INVENTION

The present invention relates to a process to obtain compounds of general formula 1 in which $R^1$ is a linear or branched (C1-C6)-alky group, an unsubstituted or substituted aryl or heteroaryl group, $R^2$ is a linear or branched (C1-C6)-alky group, an arylalkyl group); $R^3$ is H, an (C1-C4)-alkyl group. All stereoisomers are included in Formula 1.

Preferred compounds of Formula 1 are those in which $R^1$ is iBu, aryl, thienyl, $R^2$ is $PhCH_2$, n-Bu and $R^3$ is H, alkyl (C1-C4).

Threo diastereoisomers of formula 1 (2R*,3S*) are preferred.

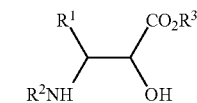

The process of this invention is depicted in Scheme 1 where the $R^1$, $R^2$ and $R^3$ groups are as indicated above.

It consists in the reaction of a substantially equimolecular amount of a silylenolester of general formula 3, where $R^4$ is Me, Et and $R^5$ is Me, Et and an imine of general formula 4 where $R^1$ is a linear or branched (C1-C6)-alky group, an arylalkyl group, an unsubstituted or substituted aryl group, a heteroaryl group, $R^2$ is a linear or branched (C1-C6)-alky group or an arylalkyl group, affording intermediates of general formula (3R*,5S*,6S*,1'S*)-5 and (3R*,5S*,6S*,1'R*)-6 where $R^1$ is a linear or branched (C1-C6)-alky group, an arylalkyl group, an unsubstituted or substituted aryl group, a heteroaryl group; $R^2$ is a linear or branched (C1-C6)-alky group, an arylalkyl group; $R^4$ is a Me or Et group. Intermediates 5 and 6 are directly transformed into isoserine derivatives of general formula (2R*,3S*)-1 and (2R*,3R*)-1' where $R^3$ is H by hydrolysis or into isoserine derivatives of general formula (2R*,3S*)-1 and (2R*,3R*)-1' where $R^3$ is an (C1-C4)-alkyl group by alcoholysis.

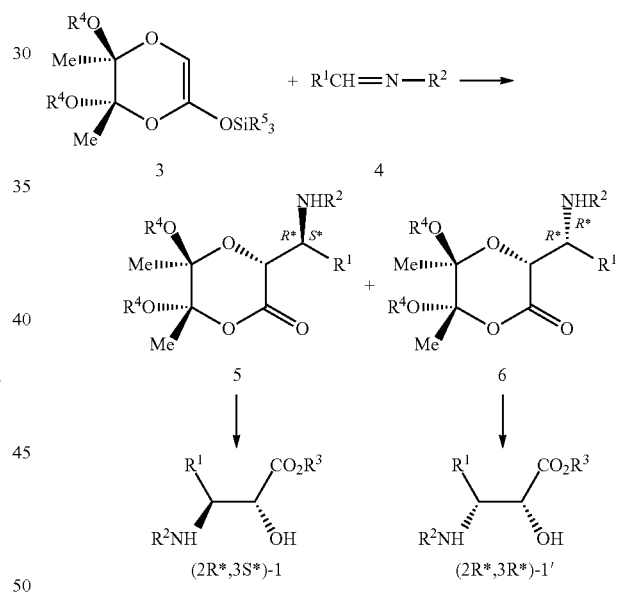

The condensation between 3 and 4 is catalyzed by both protic and Lewis acids (0.1-1 eq).

Representative Lewis catalysts are $ZnCl_2$, $CoCl_2$, $InCl_3$, $NbCl_5$, $Eu(OTf)_3$, $PdCl_2$, $SnCl_2$ and $MgBr_2$. The distribution of the products 5 and 6, and hence of the products (2R*,3S*)-1 and (2R*,3R*)-1', has shown to be dependent from the kind of the Lewis acid.

Lewis acids such as $InCl_3$ and $SnCl_2$ and $MgBr_2$ afford both the better threo diastereoselection (i.e. increase the formation of the preferred diasteromer (2R*,3S*)-1) and the higher reaction yield. Accordingly, $InCl_3$, $SnCl_2$ ans $MgBr_2$ are preferred.

The reaction can be performed in an ample range of temperatures, i.e. from −70° C. to 25° C. Best results were obtained between −40 and −30° C. This range is thus preferred.

The reaction occurs advantageously in aprotic polar solvents as, for example, dimethylformamide, acetonitrile, dichloromethane, chloroform, tetrahydrofuran. Acetonitrile and dichloromethane are preferred.

If necessary, all products can be purified using standard procedures.

Alcoholysis is performed using a proper alcohol $R^3OH$ in presence of trimethylsilyl chloride.

According to a preferred form of the invention, which affords the best results as to yields and diastereoselection, the reaction is performed as "one pot reaction" that avoids the isolation of all intermediates and gives the final pure threo diastereoisomers after a simple crystallization step.

According to this process, imine 4 is first generated in situ from the aldehyde ($R^1CHO$) and an amine ($R^2NH_2$, where $PhCH_2NH_2$ is preferred) in acetonitrile at room temperature and in presence of molecular sieves or by distillation of the azeotropic mixture acetonitrile/water. The reaction temperature is lowered at −30° C. and the silyl derivative 3 is added. Then the catalyst is added and the mixture stirred for 1 h. The crude reaction mixture is directly treated with a solution of trimethylsilyl chloride in alcohol and the pure diastereoisomer (2R*,3S*)-1 (where $R^3$ is an (C1-C4)-alkyl group) is isolated after crystallization.

If desired, the method of the present invention can afford directly enantiopure compounds (thus avoiding the resolution step) by starting from enantiopure compound 3 ($R^4$=Me, $R^5$=Et).

Compounds 3 are obtained from the corresponding lactones 2 according to Scheme 2.

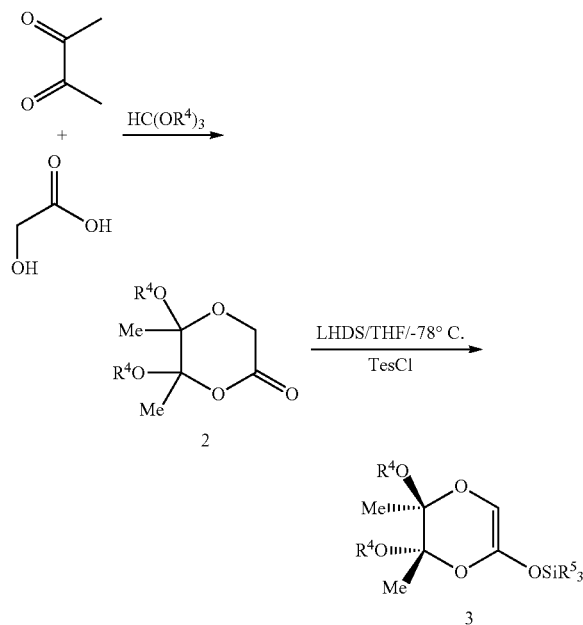

Compound 2 ($R^4$=Me) is a known compounds which can be obtained by a conventional method[8c]. Compounds 2 ($R^4$=Et), 3 ($R^4$=Me, $R^5$=Et), 3 ($R^4$=$R^5$=Et) are new compounds which are also part of the present invention together with their method of preparation. The new lactone 2 ($R^4$=Et) is prepared through a very efficient "one pot" protocol starting directly from a mixture of 2,3-butandione, glycolic acid and ethyl orthoformate in presence of a catalytic amount of $H_2SO_4$. Compounds 3 are prepared in excellent yield from 2 by using lithium hexamethylenedisilylamide (LHMDS) in THF at −78° C. and $Et_3SiCl$ as silylating agent (Scheme 2). Short reaction times are advantageous.

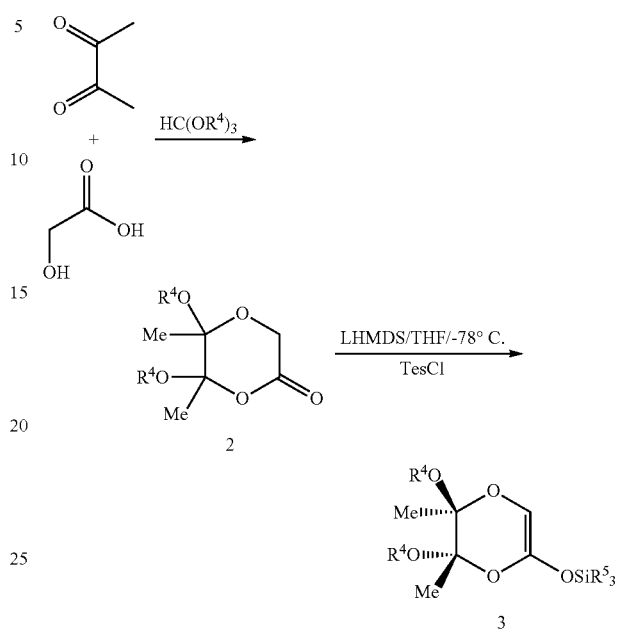

According to a preferred feature of the present invention the imines 4 are prepared in situ from the corresponding aldehyde and amine and the reaction mixture is immediately made to react with compounds 3 thus avoiding their isolation which is troublesome and yield-lowering because imines are known to be rather instable compounds.

ADVANTAGES OF THE INVENTION

The method of the present invention is superior because of the simplicity of the procedure which does not require any isolation of the intermediates as well as of troublesome chromatographic purifications.

Mild conditions are needed to deprotect both the hydroxy and the carboxy groups. This is important because the risk of racemization is fully avoided. Good yields and diastereoselection are a further essential advantage.

The present process affords a racemic mixture of isoserine derivatives which can be separated by conventional procedures. However, if desired, the resolution step is easily avoided and enantiopure compounds are obtained directly if enantiopure protected glycidic acid[10] is used.

EXAMPLES $InCl_3$ was previously anhydrified at 200° C. under vacuum for 2 h.

5,6-Diethoxy-5,6-dimethyl-[1,4]-dioxan-2-one 2,3-Butandione (4.6 mL, 46.22 mmol) and glycolic acid (3.07 g, 40.40 mmol) were dissolved in ethyl orthoformate (40 mL) and a catalytic amount of $H_2SO_4$ was added. The reaction mixture was stand at 25° C. for 1 h. A saturated solution of $NaHCO_3$ (10 mL) was added and the mixture was extracted with AcOEt (3×30 mL). The organic layers were anhydrified over $Na_2SO_4$ and the crude reaction mixture was chromatographed on silica gel (cyclohexane/AcOEt, 10:1)

affording pure compound 2 (R⁴=Et, 52%) after crystallization. White solid, mp 37° C. (CH₂Cl₂/pentane, 0° C.). IR (NaCl) $v_{max}$ 1752 cm⁻¹; ¹H NMR (CDCl₃) δ 4.32, 4.23 (AB system, J 16.6, 2H), 3.79-3.69 (m, 2H), 3.58 (q, J 7.2, 2H), 1.53 (s, 3H), 1.41 (s, 3H), 1.21 (t, J 6.9, 3H), 1.99 (t, J 7.0, 3H); ¹³C NMR (CDCl₃) δ 168.1, 105.2, 97.8, 60.5, 58.8, 57.3, 18.8, 17.9, 15.9, 15.7, 15.3. MS (ESI) m/z 341.4 [M+23]⁺; Anal calcd for C₁₀H₁₈O₅: C, 55.03; H, 8.31; found C, 55.12; H, 8.38.

5,6-Dimethoxy-5,6-dimethyl-[1,4]-dioxen-2-yloxy) triethylsilane

Lactone 2 (R⁴=Me) (3.23 g, 17 mmol) was dissolved in anhydrous THF
(35 mL) and the mixture was cooled to −78° C. under N₂. LHMDS (4.52 g, 27 mmol) was dissolved in THF (10 mL) and then added dropwise. After addition, the mixture was stirred for another 10 min before addition of TESCl (4 mL, 26 mmol). The resulting solution was then allowed to warm to 25° C. and the stirring was continued overnight. THF was then removed under reduced pressure, and pentane (50 mL) were added to the residue. The resulting suspension was filtered through Celite, and the solvent was removed in vacuo affording the crude compound that was distilled under vacuum (120° C., 0.8 mmHg). Pure compound 3 (R⁴=Me, R⁵=Et) was obtained (4.26 g, 82%) as a colorless oil. IR (NaCl) $v_{max}$ 1719, 1149, 740 cm⁻¹; ¹H NMR (CDCl₃) δ 5.52 (s, 1H), 3.37 (s, 1H), 3.22 (s, 1H), 1.45 (s, 3H), 1.38 (s, 3H), 1.06-0.94 (m, 9H), 0.75-0.67 (m, 6H); ¹³C NMR (CDCl₃) δ 143.9, 104.3, 96.6, 90.4, 49.5, 48.6, 17.6, 17.1, 6.6, 4.8. MS (ESI) m/z 218.9; Anal calcd for C₁₄H₂₈O₅Si: C, 55.23; H, 9.27; found C, 55.11; H, 9.15.

5,6-Diethoxy-5,6-dimethyl-[1,4]-dioxin-2-yloxy) triethylsilane

Silyl derivative 3 (R⁴=R⁵=Et) (4.8 g, 85%) was prepared according to the above synthetic protocol, but the base was added to the mixture of 2 (R⁴=Et) (3.7 g, 17 mmol) and TESCl. Colorless oil (130° C., 0.8 mmHg). IR (NaCl) $v_{max}$ 1721, 1149, 744 cm⁻¹; ¹H NMR (CDCl₃) δ 5.50 (s, 1H), 3.68-3.63 (m, 2H), 3.51 (q, J 7.0, 2H), 1.46 (s, 3H), 1.40 (s, 3H), 1.22-1.03 (m, 6H), 1.02-0.88 (m, 9H), 0.75-0.63 (m, 4H), 0.55 (q, J 10.8, 2H); ¹³C NMR (CDCl₃) δ 143.8, 104.3, 100.2, 96.4, 57.4, 56.6, 18.4, 17.9, 15.9, 15.7, 6.6, 4.9. MS (ESI) m/z 355.2 [M+23]⁺; Anal calcd for C₁₆H₃₂O₅Si: C, 57.79; H, 9.70; found C, 57.60; H, 9.58.

Preparation of Compounds 5 and 6

Method A.
Imine 4 (0.66 mmol) was dissolved in dry MeCN (1.2 mL) under nitrogen and stirring. The reaction mixture was than cooled at −30° C. and anhydrous InCl₃ (73 mg, 0.33 mmol) was added in one portion. After stirring at this temperature for 10 min, a solution of silyl derivative 3 (0.66 mmol) in dry MeCN (1 mL) was added dropwise. The reaction mixture was stirred for 1 h and than quenched with a saturated solution of NaHCO₃ (1 mL). The crude material was extracted with AcOEt (3×5 mL) and the collected organic phases were washed with brine, dried over Na₂SO₄, filtered and the solvent was removed under vacuum. The crude material was purified by silica gel flash chromatography. Compounds 5/6 (R⁴=Et) were chromatographed by a flash Cartridge chromatography (SiO₂; n-hexane/Et₂O, 7:2; flow: 30 mL/min). In these last cases, only isomers 5 were isolated. Method B.

Operating in a two necked round bottomed flask equipped with a magnetic stirring bar and a nitrogen inlet, the proper aldehyde (benzaldehyde: 60 µL, 0.59 mmol; isovaleraldehyde: 63 µL, 0.59 mmol) and amine (benzylamine: 79 µL, 0.59 mmol) were dissolved in MeCN (1.5 mL) in the presence of molecular sieve (60 mg, activated at 200° C. under vacuum for 2 h). After 1 h, the reaction mixture was cooled at −30° C. and anhydrous InCl₃ (65.3 mg, 0.29 mmol) was added in one portion. After stirring at this temperature for 10 min, a solution of silyl enol ether 3 (R⁴=Me, R⁵=Et) (180.2 mg, 0.59 mmol) in dry MeCN (1 mL) was added dropwise. The reaction mixture was stirred for 1 h. The reaction mixture was worked up as reported in the above procedure and compounds 5/6 (R¹=Ph, R²=Bn, R⁴=Me) or 5/6 (R¹=Me₂CHCH₂, R²=Bn, R⁴=Me) were isolated, respectively.

(3R*,5S*,6S*)-3-(1'-N-Benzylamino-1'-phenyl-methyl)-5,6-dimethoxy-5,6-dimethyl-[1,4]-dioxan-2-one (5,6: R¹=Ph, R²=Bn, R⁴=Me). Column chromatography: AcOEt/cyclohexane, 1:5; Method A: 65% (4:1), 5: 52%, 6: 13%. Method B: 5: 71%, 6: 16%.

1'S*-5

(R¹=Ph, R²=Bn, R⁴=Me): 108° C. (n-pentane/CH₂Cl₂). IR (KBr) $v_{max}$ 3372, 1744 cm⁻¹; ¹H NMR (CDCl₃) δ 7.40-7.22 (m, 10H), 4.31, 4.28 (AB system, J 2.9, 2H), 3.60, 3.51 (AM system, J 13.2, 2H), 3.21 (s, 3H), 3.14 (s, 3H), 3.00-2.00 (br, 1H, exch.), 1.47 (s, 3H), 1.37 (s, 3H); ¹³C NMR (CDCl₃) δ 169.2, 140.8, 139.7, 128.7, 128.6, 128.5, 127.2, 105.1, 98.6, 75.7, 63.6, 51.1, 50.1, 49.5, 18.4, 17.2. MS (ESI) m/z 386.0 [M+1]⁺; Anal calcd for C₂₂H₂₇NO₅: C, 68.55; H, 7.06; N, 3.63; found C, 68.43; H, 7.14; N, 3.56.

1'R*-6

(R¹=Ph, R²=Bn, R⁴=Me): pale yellow oil. IR (NaCl) $v_{max}$ 3318, 1748 cm⁻¹; ¹H NMR (CDCl₃) δ 7.41-7.26 (m, 10H), 4.54, 4.30 (AB system, J 2.7, 2H), 3.75, 3.56 (AM system, J 13.2, 2H), 3.33 (s, 3H), 2.77 (s, 3H), 2.76 (brs, 1H, exch.), 1.37 (s, 3H), 1.36 (s, 3H); ¹³C NMR (CDCl₃) δ 168.1, 140.5, 138.4, 129.7, 128.7, 128.2, 127.8, 127.4, 105.1, 98.6, 74.7, 63.4, 51.5, 49.6, 49.5, 18.3, 17.2. MS (ESI) m/z 386.2 [M+1]⁺; Anal calcd for C₂₂H₂₇NO₅: C, 68.55; H, 7.06; N, 3.63; found C, 68.40; H, 7.15; N, 3.51.

(3R*,5S*,6S*)-3-(1'-N-Benzylamino-3'-methyl-butyl)-5,6-dimethoxy-5,6-dimethyl-[1,4]-dioxan-one (5,6: R¹=Me₂CHCH₂, R²=Bn, R⁴=Me). Column chromatography: compounds 5 and 6 are instable when chromatographed on silica gel (AcOEt/cyclohexane, 1:5) with a low flow aiming to separate the two isomers, and a drammatic decrease of the yield was observed. For this reason, only the major isomer 5 (R¹=Me₂CHCH₂, R²=Bn, R⁴=Me) was isolated in pure form. Alternatively, when the crude reaction mixture was chromatographed on neutral alumine (cyclohexane/Et₂O, 7:1) the mixture of compounds was obtained good yield. Method A: 74%.

1'S*-5

(R¹=Me₂CHCH₂, R²=Bn, R⁴=Me): pale yellow oil. IR (NaCl) $v_{max}$ 3339, 1747 cm⁻¹; ¹H NMR (CDCl₃) δ 7.37-7.19 (m, 5H), 4.17 (d, J 2.6, 1H), 3.78 (s, 2H), 3.28-3.24 (m, 1H), 3.28 (s, 3H), 3.24 (s, 3H), 1.90 (brs, 1H, exch.), 1.80-1.60 (m, 1H), 1.50-1.38 (m, 2H), 1.46 (s, 3H), 1.37 (s, 3H), 0.91 (d, J 6.6, 3H), 0.86 (d, J 6.3, 3H); $^{13}$C NMR (CDCl$_3$) δ 170.1, 141.2, 128.5, 128.3, 126.9, 105.0, 98.3, 72.5, 57.5, 51.8, 50.1, 49.3, 40.8, 25.4, 23.0, 22.98, 18.2, 17.1. Anal calcd for C$_{20}$H$_{31}$NO$_5$: C, 65.73; H, 8.55; N, 3.83; found C, 65.60; H, 8.70; N, 3.71.

(3R*,5S*,6S*)-3-(1'-N-n-Butyl-1'-phenyl-methyl)-5,6-dimethoxy-5,6-dimethyl-[1,4]-dioxan-2-one (5,6: R$^1$=Ph, R$^2$=Me(CH$_2$)$_3$, R$^4$=Me). Column chromatography: AcOEt/cyclohexane, 1:5; Method A: 68% (3.2:1), 5: 52%, 6: 16%.

1'S*-5

(R$^1$=Ph, R$^2$=Me(CH$_2$)$_3$, R$^4$=Me): pale yellow oil. IR (NaCl) ν$_{max}$ 3343, 1755 cm$^{-1}$; $^1$H NMR (CDCl$_3$) δ 7.33-7.21 (m, 5H), 4.26, 4.22 (AB system, J 2.7, 2H), 3.31 (s, 3H), 3.11 (s, 3H), 2.55-2.20 (m, 3H, 1H exch.), 1.55-1.20 (m, 4H), 1.44 (s, 3H), 1.35 (s, 3H), 0.83 (t, J 7.0, 3H); $^{13}$C NMR (CDCl$_3$) δ 169.2, 139.9, 128.3, 128.2, 127.3, 104.9, 98.4, 75.5, 63.9, 49.9, 49.3, 46.7, 32.6, 20.5, 18.1, 17.0, 14.2. MS (ESI) m/z 352.1 [M+1]$^+$; Anal calcd for C$_{19}$H$_{29}$NO$_5$: C, 64.93; H, 8.32; N, 3.99; found C, 64.80; H, 8.47; N, 3.87.

1'R*-6

(R$^1$=Ph, R$^2$=Me(CH$_2$)$_3$, R$^4$=Me): pale yellow oil. IR (NaCl) ν$_{max}$ 3323, 1747 cm$^{-1}$; $^1$H NMR (CDCl$_3$) δ 7.37-7.24 (m, 5H), 4.53, 4.24 (AB system, J 3.5, 2H), 3.32 (s, 3H), 2.75 (s, 3H), 2.75-2.40 (m, 3H, 1H exch.), 1.60-1.20 (m, 4H), 1.35 (s, 3H), 1.33 (s, 3H), 0.86 (t, J 7.1, 3H); $^{13}$C NMR (CDCl$_3$) δ 168.1, 138.4, 129.4, 127.5, 127.4, 104.9, 98.5, 74.0, 63.7, 49.4, 49.3, 47.2, 32.3, 20.6, 18.1, 17.0, 14.2. MS (ESI) m/z 352.1 [M+1]$^+$; Anal calcd for C$_{19}$H$_{29}$NO$_5$: C, 64.93; H, 8.32; N, 3.99; found C, 64.78; H, 8.43; N, 3.88.

(3R*,5S*,6S*,1'S*)-3-(1'-N-Benzylamino-1'-phenyl-methyl)-5,6-diethoxy-5,6-dimethyl-[1,4]-dioxan-2-one (5: R$^1$=Ph, R$^2$=Bn, R$^4$=Et). Method A: 74%; Mp 154° C., dec. (CH$_2$Cl$_2$/Et$_2$O). IR 3344, 1749 cm$^{-1}$; $^1$H NMR (CDCl$_3$) δ 7.38-7.17 (m, 10H), 4.30, 4.23 (AB system, J 2.5, 2H), 3.66, 3.43 (AM system, J 13.2, 2H), 3.73-3.19 (m, 4H), 3.00-2.00 (br, 1H, exch.), 1.49 (s, 3H), 1.38 (s, 3H), 1.06 (t, J 6.9, 3H), 0.87 (t, J 6.9, 3H); $^{13}$C NMR (CDCl$_3$) δ 169.2, 140.5, 139.7, 128.6, 128.5, 128.4, 128.3, 127.5, 127.0, 105.0, 98.2, 75.5, 63.2, 58.3, 57.3, 50.8, 18.9, 17.7, 15.2, 15.1. MS (ESI) m/z 414.0 [M+1]$^+$; Anal calcd for C$_{24}$H$_{31}$NO$_5$: C, 69.71; H, 7.56; N, 3.39; found C, 69.58; H, 7.68; N, 3.27.

(3R*,5S*,6S*1'S*)-3-(1'-N-Benzylamino-1'-(3,4-methylenedioxy)phenyl-methyl)-5,6-diethoxy-5,6-dimethyl-[1,4]-dioxan-2-one (5: R$^1$=Ph, R$^2$=3,4-OCH$_2$O-Ph, R$^4$=Et). 87%. Mp 112° C. (n-pentane/CH$_2$Cl$_2$); IR (NaCl) ν$_{max}$ 3459, 1736 cm$^{-1}$; $^1$H NMR (CDCl$_3$) δ 7.26-7.22 (m, 5H), 6.94 (s, 1H), 6.77 (s, 2H), 5.98 (s, 2H), 4.18 (brs, 2H), 3.65, 3.42 (AM system, J 13.2, 2H), 3.78-3.20 (m, 4H), 2.55-1.80 (br, 1H, exch.), 1.49 (s, 3H), 1.40 (s, 3H), 1.09 (t, J 7.0, 3H), 0.88 (t, J 7.0, 3H); $^{13}$C NMR (CDCl$_3$) δ 169.0, 147.9, 147.0, 140.5, 133.9, 128.6, 128.3, 127.0, 122.0, 108.6, 108.1, 104.9, 101.1, 98.2, 75.6, 62.9, 58.3, 57.4, 50.6, 18.9, 17.8, 15.2, 15.0. MS (ESI) m/z 458.1 [M+1]$^+$; Anal calcd for C$_{25}$H$_{31}$NO$_7$: C, 65.63; H, 6.83; N, 3.06. found C, 65.45; H, 7.00; N, 2.96.

General Procedure for the Methanolysis of Compounds 5 and 6

Compound 5 (R$^1$=Ph, R$^2$=Bn, R$^4$=Me; R$^1$=Ph, R$^2$=Bn, R$^4$=Et) or 6 (R$^1$=Ph, R$^2$=Bn, R$^4$=Me) (0.225 mmol) was dissolved in a 0.5 M solution of TMSCl in MeOH (1.0 ml, 0.5 mmol) under stirring at 25° C. for 10 min. The solvent was eliminated and the residue was crystallized giving pure compound 1 or 1' (R$^1$=Ph, R$^2$=Bn) [1: 97% from 5 (R$^1$=Ph, R$^2$=Bn, R$^4$=Me); 1: 95% from 5 (R$^1$=Ph, R$^2$=Bn, R$^4$=Et); 1': 80% from 6 (R$^1$=Ph, R$^2$=Bn, R$^4$=Me).

"One pot" Preparation of Methyl 3-(Amino)-2-hydroxy-propionate Derivatives 1/1'

Method C): the reaction between 4 (R$^1$=Ph, R$^2$=Bn) and 3 (R$^4$=R$^5$=Et) was performed according to the general procedure. The $^1$H NMR analysis of the crude reaction mixture showed the presence of the diastereoisomer 5 (R$^1$=Ph, R$^2$=Bn, R$^4$=Et) and only trace amount of 6 (R$^1$=Ph, R$^2$=Bn, R$^4$=Et) (HPLC: ASCENTIS SI 150×4.6 mm, 3 μm, 0.8 mL/min, λ=210 nm, n-hexane/iPrOH, 98:2; 92:8). The crude reaction mixture was treated with MeOH/TMSCl according to the above reported procedure and methyl ester derivative 1 (R$^1$=Ph, R$^2$=Bn, R$^3$=Me) (60%) was obtained after recrystallization. A further crop of compound 1 (R$^1$=Ph, R$^2$=Bn, R$^3$=Me; 10%) was isolated after column chromatography on silica gel (cyclohexane/AcOEt, 4:1). Method D): Operating under nitrogen, the proper aldehyde (0.59 mmol) and benzylamine (79 μL, 0.59 mmol) were dissolved in MeCN (1.5 mL) in the presence of molecular sieve (60 mg, activated at 200° C. under vacuum for 2 h) and the mixture was stirred for 1 h. Alternatively, the imine 4 was generated in MeCN after which the azeotropic mixture MeCN/H$_2$O was evaporated. MeCN was added (2 mL) and the mixture was stirred for 10 min and the solvent evaporated. The same protocol was repeated and finally MeCN (1.5 mL) was added. The reaction mixture was cooled at −30° C., then compound 3 (R$^4$=R$^5$=Et) (0.59 mmol) and the catalyst (InCl$_3$ or MgBr$_2$, 0.29 mmol) were added and the stirring continued for 1 h. The crude reaction mixture was treated with MeOH/TMSCl according to the above reported procedure for the methanolysis and methyl ester derivatives 1 were isolated after crystallization or after flash silica gel column chromatography.

Methyl 3-(Benzylamino)-2-hydroxy-3-phenyl-propionate d.e. 83% (column chromatography (AcOEt/cyclohexane, 1:4). (2R*,3S*): 74%. Mp 107° C. (n-pentane/Et$_2$O), (107-108° C.)[9]. $^1$H NMR (CDCl$_3$) δ 7.41-7.22 (m, 10H), 4.26, 3.95 (AX system, J 4.1, 2H), 3.77, 3.49 (AM system, J 13.2, 2H), 3.70 (s, 3H), 3.00-2.00 (br, 2H, exch.). (2R*,3R*): 10%. Mp 99° C. (n-pentane/CH$_2$Cl$_2$), (98-99° C.)[9]. $^1$H NMR (CDCl$_3$) δ 7.38-7.22 (m, 10H), 4.54, 4.06 (AX system, J 4.0, 2H), 3.78, 3.61 (AM system, J 12.8, 2H), 3.60 (s, 3H), 3.00-2.00 (br, 2H, exch.).

Methyl 3-(Benzylamino)-2-hydroxy-3-(4-nitrophenyl)-propionate d.e. 83% (column chromatography: AcOEt/cyclohexane, 1:3). (2R*,3S*): 74%. Mp 147-149° C. (n-hexane/CH$_2$Cl$_2$). IR (KBr) ν$_{max}$ 3491, 1729 cm$^{-1}$; $^1$H NMR (CDCl$_3$) δ 8.23, 7.53 (AA'XX' system, J 8.8, 4 H), 7.38-7.10 (m, 5H), 4.25, 4.06 (AM system, J 3.3, 2H), 3.76, 3.43 (AM system, J 13.5, 2H), 3.75 (s, 3H), 3.20-2.00 (brs, 2H, exch.). $^{13}C$ NMR (CDCl$_3$) δ 173.4, 147.9, 147.6, 139.6, 128.9, 128.5, 128.3, 127.4, 123.9, 74.6, 62.9, 52.8, 50.8. MS (ESI+) m/z 353.1.

Methyl 3-(Benzylamino)-2-hydroxy-3-(4-methoxyphenyl)-propionate d.e. 83%. Column chromatography (AcOEt/cyclohexane, 1:3). (2R*,3S*): 72%. IR (KBr) ν$_{max}$ 3491, 1733 cm$^{-1}$; $^1H$ NMR (CDCl$_3$) δ 7.40-7.18 (m, 7H), 6.90 (d, J 8.8, 2 H), 4.22, 3.89 (AM system, J 4.1, 2H), 3.82 (s, 3H), 3.75, 3.47 (AM system, J 13.2, 2H), 3.70 (s, 3H), 2.80-1.90 (brs, 2H, exch.).

Methyl 3-(Benzylamino)-2-hydroxy-3-(4-chlorophenyl)-propionate d.e. 82%. Column chromatography (AcOEt/cyclohexane, 1:4). (2R*,3S*): 73%. Mp 106-108° C. (n-hexane/CH$_2$Cl$_2$). IR (KBr) ν$_{max}$ 3491, 1729 cm$^{-1}$; $^1H$ NMR (CDCl$_3$) δ 7.40-7.10 (m, 9H), 4.21, 3.91 (AM system, J 3.6, 2H), 3.71 (s, 3H), 3.75, 3.45 (AM system, J 14.5, 2H), 3.70 (s, 3H), 2.80-1.90 (brs, 2H, exch.).

Methyl 3-(Benzylamino)-2-hydroxy-5-methyl-hexanoate d.e. 87% (column chromatography: Et$_2$O/n-hexane, 1:4). (2R*,3S*): 68%. Mp 89-90° C. IR (NaCl) ν$_{max}$ 3467, 1739 cm$^{-1}$; $^1H$ NMR (CDCl$_3$) δ 7.40-7.20 (m, 5H), 4.05 (d, J 2.2, 2H), 3.80-3.60 (2H, overl.), 3.73 (s, 3H), 3.03 (dt, J 7.0, 1.8, 1H), 2.50-2.05 (br, 2H, exch.), 1.80-1.60 (m, 1H), 1.50-1.20 (m, 2H), 0.92 (d, J 1.8, 3H), 0.86 (d, J 1.8, 3H); $^{13}C$ NMR (CDCl$_3$) δ 175.3, 140.5, 128.5, 128.4, 127.3, 72.0, 57.4, 52.3, 52.0, 41.6, 25.3, 23.0, 22.7. MS (ESI+) m/z 266.1.

Methyl 3-(Benzylamino)-2-hydroxy-3-tiophenyl-propionate d.e. 79% (column chromatography AcOEt/cyclohexane, 1:4). (2R*,3S*): 73%. Oil. IR (NaCl) ν$_{max}$ 3467, 1739 cm$^{-1}$; $^1H$ NMR (CDCl$_3$) δ 7.38-7.20 (m, 6H), 7.03-6.95 (m, 2H), 4.33, 4.22 (AB system, J 3.7, 2H), 3.83, 3.55 (AM system, J 13.5, 2H), 3.74 (s, 3H), 3.00-2.00 (br, 2H, exch.); $^{13}C$ NMR (CDCl$_3$) δ 173.6, 143.6, 140.0, 128.5, 128.4, 127.3, 126.6, 126.0, 125.3, 75.2, 59.2, 52.7, 50.8. MS (ESI+) m/z 314.1.

REFERENCES

1. Matthijs, S.; Budzikiewicz, H.; Schafer, M.; Wathelet, B.; Cornelis, P. *Zeitschrift fuer Naturforschung, C: J. Biosc.* 2008, 63, 8-12. *Chem. Abstr.* 2008, 149, 489268.
2. Iizuka, K.; Kamijo, T.; Harada, H.; Akahane, K.; Kubota, T.; Umeyama, H.; Ishida, T.; Kiso Y. *J. Med. Chem.* 1990, 33, 2707-2714.
3. Blomgren, H.; Wasserman, J. *Cancer Lett.* 1981, 11, 303-308.
4. Okino, T.; Matsuda, H.; Murakami, M.; Yamaguchi, K. *Tetrahedron Lett.* 1993, 34, 501-504.
5. Shimamoto, K. *Chem. Rec.* 2008, 8, 182-199.
6. (a) Bodkin, J. A.; Bacskay, G. B.; McLeod, M. D. *Org. Biomol. Chem.* 2008, 6, 2544-2553. (b) Cariou, C: C. A.; Clarkson, G: Shipman, M. *J. Org. Chem.* 2008, 73, 9762-9764. (c) Chen, J.; Kuznetsova, L. V.; Ungreanu, I. M.; Ojima, I. In *Enantioselective Synthesis of β-Amino Acids* (2nd Ed.) Juaristi, E.; Soloshonok, V. A., Eds. John Wiley & Sons, Inc., Hoboken, N.J. 2005, 447-476. (d) Spletstoser, J. T.; Flaherty, P. T.; Himes, R. H.; Georg, G. I. *J. Med. Chem.* 2004, 47, 6459-6465. (e) Martin-Zamora, E.; Ferrete, A.; Llera, J. M.; Munoz, J. M.; Pappalardo, R. R.; Fernandez, R.; Lassaletta, J. M. *Chem. Eur. J.* 2004, 10, 6111-6129. (f) Liu, C.; Tamm, M.; Notzel, M. W.; de Meijere, A.; Schilling, J. K.; Kingston, D. G. I. *Tetrahedron Lett.* 2003, 44, 2049-2052. (g) Bunnage, E. M.; Davies, S. G.; Goodwin, C. J. *J. Chem. Soc. Perkin* 1 1994, 2385-2391.
7. (a) Ke, B.; Qin, Y.; Zhao, F.; Qu, Y. *Bioorg. Med. Chem. Lett.* 2008, 18, 4783-4785. (b) Wang, Y.; He, Q.-F.; Wang, H.-W.; Zhou, X.; Huang, Z.-Y.; Qin, Y. *J. Org. Chem.* 2006, 71, 1588-1591. (c) Hata, S.; Tomioka, K. *Tetrahedron* 2007, 63 8514-8520. (d) Ha, H.-J.; Ahn, Y.-G.; Woo, J.-S.; Lee, G. S.; Lee, W. K. *Bull. Chem. Soc. Jap.* 2001, 74, 1667-1672 (e) Guo, Z.; Shi, T.; Jiang, J.; Yang, L.; Hu, W. *Org. Biomol. Chem.* 2009, 7, 5028-5033.
8. Ley, S. V.; Diez, E.; Dixon, D. J.; Guy, R. T.; Michel, P.; Nattrass, G. L.; Sheppard, T. D. *Org. Biomol. Chem.* 2004, 2, 3608-3617.
9. Feske, B. D.; Kaluzna, I. A.; Stewart, J. D. *J. Org. Chem.* 2005, 70, 9654-9657.
10. Diez, E.; Dixon, D. J.; Ley, S. V. *Angew. Chem. Int. Ed.* 2001, 40, 2906-2909.

The invention claimed is:

1. A process for the preparation of compounds of general formula 1

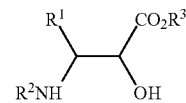

in which R$^1$ is a linear or branched (C1-C6)-alky group, an unsubstituted or substituted aryl or heteroaryl group, R$^2$ is a linear or branched (C1-C6)-alky group, an arylalkyl group); R$^3$ is H, a (C1-C4)-alkyl group, comprising:
reacting a silylenolester of general formula 3, where R$^4$ is Me, Et and R$^5$ is Me, Et with an imine of general formula 4 where R$^1$ is a linear or branched (C1-C6)-alky group, an arylalkyl group, an unsubstituted or substituted aryl group, a heteroaryl group, R$^2$ is a linear or branched (C1-C6)-alky group or an arylalkyl group to obtain intermediates of general formula (3R*,5S*,6S*,1'S*)-5 and (3R*,5S*,6S*,1'R*)-6; and alcoholyzing or hydrolyzing the obtained intermediates of general formula (3R*,5S*,6S*,1'S*)-5 and (3R*, 5S*,6S*,1'R*)-6 where R$^1$ is a linear or branched (C1-C6)-alky group, an arylalkyl group, an unsubstituted or substituted aryl group, a heteroaryl group; R$^2$ is a linear or branched (C1-C6)-alky group, an arylalkyl group; R$^4$ is a Me or Et group

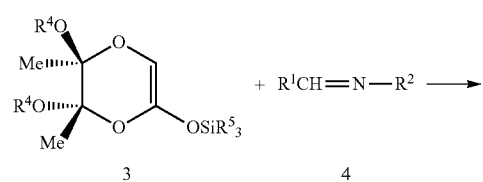

-continued

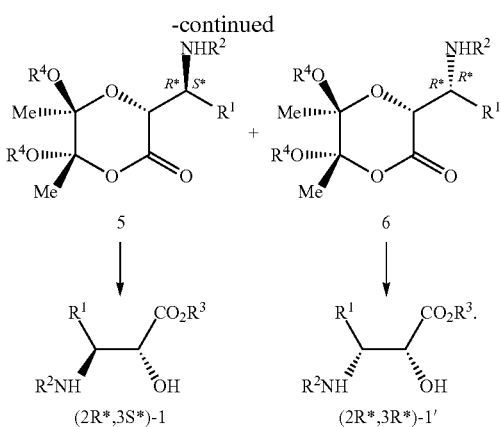

2. A process according to claim 1 wherein the reacting step between compounds 3 and 4 is catalyzed by protic or Lewis acids.

3. A process according to claim 2 wherein the reacting step is catalyzed by Lewis acids selected from $InCl_3$ and $SnCl_2$ and $MgBr_2$.

4. A process according to claim 2 wherein the reacting step temperature is in the range from −40 to −30° C.

5. A process according to claim 2 wherein the reacting step is carried out in aprotic polar solvents selected from dimethylformamide, acetonitrile, dichloromethane, chloroform, tetrahydrofuran, preferably Acetonitrile and dichloromethane.

6. A process according to claim 1 wherein the alcoholyzing step is performed using an alcohol $R^3OH$ in presence of trimethylsilyl chloride.

7. A process according to claim 1 which is performed as "one pot reaction" without isolating the intermediates to give the final pure threo diastereoisomers by crystallization.

8. A process according to claim 7 comprising:
generating in situ imine 4 from the aldehyde ($R^1CHO$) and an amine ($R^2NH_2$), in acetonitrile at room temperature and in presence of molecular sieves or by distillation of the azeotropic mixture acetonitrile/water;
adding silyl derivative 3 at −30° C. followed by addition of the catalyst to obtain a crude reaction mixture; and
treating the crude reaction mixture with trimethylsilyl chloride in alcohol and isolation of the pure diastereoisomer (2R*,3S*)-1 (where $R^3$ is an (C1-C4)-alkyl group) after crystallization.

9. A process according to claim 8, wherein said amine is $PhCH_2NH_2$.

* * * * *